United States Patent [19]
DeMarco et al.

[11] 4,190,655
[45] Feb. 26, 1980

[54] AMILORIDE CITRATE

[75] Inventors: Joseph DeMarco, Hatfield; Gerald S. Brenner, Norristown, both of Pa.

[73] Assignee: Merck & Co., Inc., Rahway, N.J.

[21] Appl. No.: 937,245

[22] Filed: Aug. 28, 1978

[51] Int. Cl.$^2$ .................. A61K 31/495; C07D 241/16
[52] U.S. Cl. ..................................... 424/250; 544/357
[58] Field of Search ................. 544/382, 357; 424/250

[56] References Cited
U.S. PATENT DOCUMENTS 3,313,813  4/1967  Cragoe, Jr. .......................... 544/382

*Primary Examiner*—Jose Tovar
*Attorney, Agent, or Firm*—Michael C. Sudol, Jr.; Harry E. Westlake, Jr.

[57] ABSTRACT

A novel salt of amiloride particularly amiloride citrate has been discovered. Because of its inherent insolubility and less bitter taste, it would lend itself to be more easily formulated into oral liquids, sustained release formulations and chewable tablets than would amiloride hydrochloride.

4 Claims, No Drawings

AMILORIDE CITRATE

BACKGROUND OF INVENTION

The drug amiloride which is commercially known as amiloride hydrochloride dihydrate is a well known potassium sparing diuretic. U.S. Pat. No. 3,313,813 which claims amiloride also discloses that it is desirable in some instances to make a salt of amiloride using a pharmaceutically acceptable acid. However, no particular mention is made of the citrate salt of amiloride to which this invention relates.

DETAILED DESCRIPTION OF THE INVENTION

This invention relates to a new salt of amiloride namely, citrate salt of amiloride. Amiloride itself which is known chemically as 3,5,-diamino-n-(aminoiminomethyl)-6-chloropyrazinecarboxamide or N-amidino-3,5-diamino-6-chloropyrazinecarboxamide and its hydrochloride dihydrate are known and described in U.S. Pat. No. 3,313,813 as mentioned above. The citrate salt of this invention has the following formula:

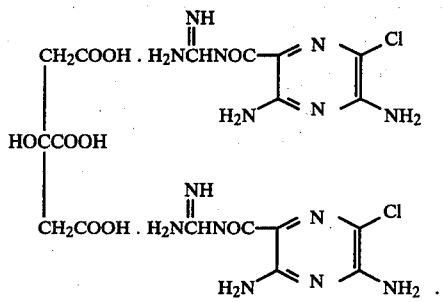

Applicant has found that this particular salt of amiloride, namely, the citrate salt of amiloride has several advantages over amiloride or amiloride hydrochloride itself. Since amiloride hydrochloride dihydrate is a soluble drug with a bitter taste, oral solutions thereof had to be flavored in order to overcome the bitter taste. The citrate salt of amiloride of the present invention can be formulated into an oral liquid as a suspension. The taste of this suspension would be much better than that of amiloride hydrochloride dihydrate in solution.

Also, to date I am aware of no sustained released formulations of amiloride hydrochloride dihydrate. Sustained release formulations can be prepared by developing a sustained release delivery system that would control the amiloride hydrochloride release. Amiloride citrate since it is relatively insoluble in water would have prolonged release properties and would possess inherent sustained release characteristics. Hence, amiloride citrate can be advantageously used in sustained release oral formulations or control release implants and insert formulations.

Further, there are no chewable tablet formulations of amiloride hydrochloride dihydrate available commercially. Because of the bitter taste of amiloride hydrochloride dihydrate, chewable tablets containing this drug would have to be flavored. Amiloride citrate, since it is relatively water insoluble would be virtually tasteless and hence, would lend itself easily to the preparation of chewable tablets which can be used, for example, in the pediatric market.

As with amiloride hydrochloride, amiloride citrate of this invention is useful because it possesses diuretic and natriuretic properties. It differs from most of the known, effective diuretic agents, however, in that it selectively enhances the excretion of sodium ions without causing an increase in excretion of potassium ions. The potassium loss, which is caused by known diuretics, often results in a severe muscular weakness. Since amiloride citrate is essentially free of this potassium depletion, it has this decided advantage as a diuretic. As a diuretic agent, it can be used for the treatment of edema, hypertension and other diseases known to be responsive to this therapy.

It has also been found as another feature of this invention that when co-administered with other diuretic agents known to enhance the elimination of potassium ions along with sodium ions, amiloride citrate will reduce the excretion of potassium ions and thus overcome this undesirable property of other diuretic agents. Amiloride citrate, therefore, is useful in combination with other classes of diuretic agents to prevent the loss of potassium which the other diuretcis otherwise would cause to be eliminated. In addition, amiloride citrate is useful by itself as a diuretic and or saluretic agent.

The amiloride citrate of this invention can be administered to patients (both human and animal) in the form of pills, tablets, capsules, elixirs, injectable preparations and the like but, particularly, in the form of oral liquids, chewable tablets, or sustained release formulations as described above. The amiloride citrate can be the only essential active ingredient of the pharmaceutical formulations or it can be combined in pharmaceutical formulations with other diuretic agents, or, indeed other therapeutic agents such as for example hydrochlorothiazide.

Amiloride citrate is advantageously administered at a dosage range of from about 5 mg/day to about 30 mg/day preferably at 5 mg/day to about 20 mg per day or at a somewhat higher or lower dosage at the physician's discretion, preferably in sub-divided amounts on a 2 to 4 times a day regimen.

Amiloride citrate can be prepared as described in Example 1. Examples 2 and 3 show typical capsule and tablet preparation using amiloride citrate.

Following are examples which illustrate the preparation of compounds and compositions falling within our invention. They should be construed as illustrations of the invention and not limitations thereof.

EXAMPLE 1

Preparation of amiloride citrate

Two millimoles of amiloride hydrochloride (604.0 mg) are dissolved in 150 ml of water, with gentle heating and filtered. One millimole of citric acid monohydrate (210.0 mg) is dissolved in 10 ml of water and added to the amiloride solution. The pH of this solution is pH 2.7. The solution is stored at 5° C. for about 24 hours. The precipitate is washed with 2 ten milliter portions of water and then dried in vacuo at 40° C. After being further dried at 65° C. for 8 hours, the resulting amiloride citrate weighed 330 mg.

| WT ppt 330 mg Dried 65° C. 8 hrs. | Theory 651 mg | | |
|---|---|---|---|
| | Theory | | Found |
| Analysis | 30.11 | N | 29.42 |
| | 33.19 | C | 32.03 |
| | 3.71 | H | 4.02 |

U.V. assay for amiloride content = 69.6%
Theory = 70.5%

EXAMPLE 2

Dry-filled capsules containing 50 mg of active ingredient per capsule

|  | Per Capsule |
|---|---|
| Amiloride citrate | 10 mg. |
| Lactose | 189 mg. |
| Magnesium Stearate | 1 mg. |
| Capsule (Size No. 3) | 200 mg. |

The amiloride citrate is reduced to a No. 60 powder and then lactose and magnesium stearate are passed through a No. 60 bolting cloth onto the powder and the combined ingredients admixed for 10 minutes and then filled into a No. 3 dry gelatin capsule.

EXAMPLE 3

Chewable Tablet containing 10 mg of active ingredient per tablet

|  | Per Tablet |
|---|---|
| Amiloride Citrate | 10 mg. |
| Starch USP | 23 mg. |
| Mannitol USP 90-100 mesh | 268 mg. |
| Starch USP (as 15% paste) | 4 mg. |
| Sugar USP Powder | 217 mg. |
| Povidone oral | 12 mg. |
| Flavors | 1 mg. |

PART A

Amiloride Citrate Granulation

Amiloride citrate and starch are mixed for 10 minutes and passed through a No. 100 mesh stainless steel screen. 40% of the mannitol is added to this mixture and the contents mixed for 10 minutes. This powder mixture is sieved through No. 80 mesh stainless steel screen.

Granulation

The resulting powder mixture of Part A is granulated with a 15% starch paste and passed through a No. 5 mesh stainless steel screen. It is dried at 50° C. for about 16 hours and then the dried granulation is sieved through a No. 20 mesh stainless steel screen.

PART B

Diluent Granulation

The remaining mannitol is mixed with the sugar for 10 minutes and the powder mixture is passed through a No. 80 mesh stainless steel screen followed by mixing for 5 minutes.

A 0.15 mg/ml solution of povidone in alcohol SD3A (denatured alcohol) is prepared and granulated with the diluent granulation of Part B already prepared above. Additional amounts of alcohol SD3A are added if necessary to prepare a good granulation. The wet granulation is passed through a No. 5 mesh stainless steel screen and the granulation is dried at 50° C for 16 hours. The dried granulation is sieved through a No. 20 mesh stainless screen.

The Part A and Part B granulations are then mixed. The dry flavors and magnesium stearate are then bolted through a No. 60 mesh screen and mixed with the blended Part A and Part B granulation for 5 minutes.

The entire mixture is then compressed with 14/32" round, flat beveled edge punch to yield the final tablets.

What is claimed is:

1. A compound of the formula:

$$\begin{array}{c} CH_2COOH \cdot H_2NCHNOC \underset{H_2N}{\overset{NH}{\|}} \underset{N}{\overset{N}{\rightleftharpoons}} \underset{NH_2}{\overset{Cl}{\searrow}} \\ | \\ HOCCOOH \\ | \\ CH_2COOH \cdot H_2NCHNOC \underset{H_2N}{\overset{NH}{\|}} \underset{N}{\overset{N}{\rightleftharpoons}} \underset{NH_2}{\overset{Cl}{\searrow}} \end{array}.$$

2. A pharmaceutical composition useful in the treatment of edema and hypertension which comprises a pharmaceutically acceptable amount of amiloride citrate and a pharmaceutically acceptable carrier.

3. A method of treating edema and hypertension which comprises administering to a patient in need of such treatment a pharmaceutically acceptable amount of amiloride citrate.

4. A method of treatment according to claim 3 wherein the amount of amiloride citrate administered is between 5 mg and 30 mg per day.

* * * * *